US005505912A

United States Patent [19]

Hallett

[11] Patent Number: 5,505,912

[45] **Date of Patent: *Apr. 9, 1996**

[54] LAMP COOLING FOR A UV LAMP REACTOR ASSEMBLY

[75] Inventor: Ronald C. Hallett, Pickering, Canada

[73] Assignee: Cryptonics Corporation, Toronto, Canada

[ * ] Notice: The term of this patent shall not extend beyond the expiration date of Pat. No. 5,372,781.

[21] Appl. No.: 336,696

[22] Filed: Nov. 7, 1994

Related U.S. Application Data

[63] Continuation-in-part of Ser. No. 836,617, Feb. 18, 1992, Pat. No. 5,372,781.

[51] Int. Cl.[6] .................................................. B01J 19/12

[52] U.S. Cl. ........................................ 422/186.3; 422/906

[58] Field of Search ................................ 422/186.3, 906

[56] References Cited

U.S. PATENT DOCUMENTS

| | | | |
|---|---|---|---|
| 3,462,597 | 8/1969 | Young | 422/186.3 |
| 3,562,520 | 2/1971 | Rippen | 250/372 |
| 3,904,363 | 9/1975 | Free | 250/431 |
| 4,002,918 | 1/1977 | Graentzel | 250/431 |
| 4,045,316 | 8/1977 | Legan | 204/157.3 |
| 4,141,830 | 2/1979 | Last | 210/748 |
| 4,179,616 | 12/1979 | Coviello et al. | 422/186.3 |
| 4,189,363 | 2/1980 | Beitzel | 204/158.2 |
| 4,694,179 | 9/1987 | Lew et al. | 250/431 |
| 4,897,246 | 1/1990 | Peterson | 422/186.3 |
| 4,952,376 | 8/1990 | Peterson | 422/186.3 |
| 4,956,098 | 9/1990 | Stevens et al. | 210/748 |
| 4,963,750 | 10/1990 | Wilson | 250/436 |
| 5,043,079 | 8/1991 | Hallett | 210/748 |
| 5,043,080 | 8/1991 | Cater et al. | 210/748 |
| 5,133,945 | 7/1992 | Hallett | 422/186.3 |
| 5,178,758 | 1/1993 | Hwang | 210/256 |
| 5,266,215 | 11/1993 | Engelhard | 210/748 |
| 5,266,280 | 11/1993 | Hallett | 422/186.3 |
| 5,277,140 | 7/1993 | Hager et al. | 422/186.3 |
| 5,372,781 | 12/1994 | Hallett et al. | 422/186.3 |

FOREIGN PATENT DOCUMENTS

| | | |
|---|---|---|
| 003879A1 | 9/1979 | European Pat. Off. . |
| 3710250 | 10/1988 | Germany . |
| WO88/04281 | 6/1988 | WIPO . |
| WO92/25502 | 12/1992 | WIPO . |

*Primary Examiner*—Donald P. Walsh
*Assistant Examiner*—Daniel Jenkins
*Attorney, Agent, or Firm*—Lowe, Price, LeBlanc & Becker

[57] ABSTRACT

This invention relates to an improved cooling system for a reactor having ultraviolet (UV) lamps, the radiation from which treats a fluid medium, for example, water, air or solvent. More particularly, the reactor system is adapted to treat contaminants in the fluids by use of UV emitting lamps which operate at high temperatures normally in excess of 300° C.

11 Claims, 3 Drawing Sheets

52 58 62 60 72 74 82 44 76 80 40 78 36 70 68 76 64 66 70 18 16 30 56 14 70 28 12 32 10 48 46 24 34 42 38 20 54 22 54 50

146
23
30
150
128
34
142
136
12(88)
134
130
144
140
138
132
134
148
152
38
154
156

92
96
88
126
106
118
84
110
124
86
104
116
102
114
122
108
112
100
94
120

90
98

LAMP COOLING FOR A UV LAMP REACTOR ASSEMBLY

This is a Continuation-in-Part of Application Ser. No. 07/836,617, filed Feb. 18, 1992, now U.S. Pat. No. 5,372, 781, entitled UV Reactor Assembly.

FIELD OF THE INVENTION

This invention relates to an improved cooling system for a reactor having ultraviolet (UV) lamps, the radiation from which treats a fluid medium, for example, water, air or solvent. More particularly, the reactor system is adapted to treat contaminants in the fluids by use of UV emitting lamps which operate at high temperatures normally in excess of 300° C.

BACKGROUND OF THE INVENTION

Ultraviolet radiation is an important workhorse in the industrial community for promoting chemical reactions, initiating chemical reactions, degrading organic and non-organic molecules, inducing mutations in biological systems, acting as an antiviral and bactericidal agent and the like. Normally the source of the ultraviolet radiation is emitted from an electric discharge lamp having various types of gases which when excited by the electric discharge, emit UV radiation. These lamps are generally categorized as low or medium/high intensity lamps. They may operate at low or high pressures for the gases within the lamps. Normally the lamps are of a quartz material which is transparent to the emitted UV radiation. The lamps may operate at low or high temperatures ranging from approximately 30° C. up to 1100° C. The power input of these lamps may range from less than 40 watts to in excess of 60,000 watts of UV radiation. The lamps may be even customized to the extent that a certain portion of the UV spectrum is omitted or enhanced rather than the entire portion of the UV spectrum.

A driving force for such variety in UV lamps is that each of the above industrial applications requires lamps having different UV intensities, different wavelength of emission, operating pressure and temperatures and power requirements.

Normally the lamps, as employed in reactor systems, particularly reactor systems which contain aqueous media, have a variety of UV transparent protective sheaths within which the lamps are placed so that the lamps do not come in contact with the material being treated by the UV radiation. This technique protects the quartz of the UV lamp and the electrical connections to the lamp electrodes. Also it can facilitate lamp replacement without having to disassemble the reactor. Two examples of this type of water treatment system are disclosed in U.S. Pat. Nos. 3,462,597 and 3,562, 520. An annular chamber is defined between the outer cylindrical wall of the water treatment apparatus and the inner sheath of the apparatus which protects the UV radiation emitting lamp from the fluids that are passed through the annular chamber in the fluid treatment apparatus. Both systems are designed so as to enclose the lamp ends as the lamp is positioned centrally of the apparatus and enclosed by the protective sheath. The sheath is of quartz or other UV transparent material. Special sheath cleaning mechanisms are described in these arrangements. The drawbacks of those systems are discussed in detail in applicant's U.S. Pat. Nos. 5,133,945 and 5,266,280.

The systems of these two earlier U.S. patents are adequate for use as an antiviral and bactericidal agent for treating drinking water. Low temperature lamps are used in accordance with standard techniques for exposing water to radiation. The lamps are totally enclosed. As demonstrated in both U.S. patents the lamp ends are completely enclosed and sealed off within the sheath. This allows replacement of air within the annular space defined between the lamp and the protective sheath with inert gases which are not oxidized by the UV radiation. This prevents the formation of ozone which is thought to be very harmful to the components used in the UV treatment systems. Completely enclosed lamps may be acceptable for systems using lamps operating at lower temperatures within the 40° to 150° C. range.

Another general approach for exposing fluids to UV radiation to initiate or expedite a desired chemical reaction within the fluids is to position a plurality of UV lamps around a reaction container having a vessel wall which is transparent to the UV radiation. This permits radiation emitted by the lamps to pass through the vessel walls and be absorbed by the fluids within the reaction container so as to initiate or expedite the desired reaction. Normally, the lamps as they surround the reaction vessel are enclosed. The enclosure may have UV reflective surfaces so as to direct radiation emitted by the lamps in a direction away from the reactor to reflect such radiation back towards the reactor. With the provision of several lamps within the enclosure overheating of the enclosed lamps can become a problem. An example of this type of reactor is discussed in U.S. Pat. No. 4,002,918.

In U.S. Pat. No. 4,897,246 and its divisional application U.S. Pat. No. 4,952,376 a UV treatment system is disclosed for decontaminating various forms of waters and waste waters. The waste waters are introduced at one end of the reactor system and by use of baffles, the waters are directed in a zigzag pattern flow over lamps within the reactor chamber. The reactor chamber is rectangular with a continuous flow of liquids through the reactor chamber. The lamps used in the system are of significantly higher power than the lamps used in the aforementioned water treatment systems of U.S. Pat. Nos. 3,462,597 and 3,562,520. In accordance with standard techniques the UV radiation emitting lamps are isolated from the fluids being treated by suitable protective sheaths. Also in accordance with standard practice the ends of the lamps are sealed off so as to define a sealed annular space between the lamp and the protective sheath. In this arrangement the preferred form of lamp used is a higher pressure mercury lamp, sometimes referred to as a medium pressure lamp. These lamps have been called both medium pressure and high pressure lamps in the literature. The operating characteristics for these lamps can vary a great deal. Lamps which we will refer to as medium pressure lamps are mercury lamps with pressures of 1 to 10 atm, with bulb temperatures greater than 300° C. and input power densities of 40 to 100 watts/cm of bulb length. These lamps operate at considerably higher temperatures than the low pressure UV lamps. Medium pressure lamps operate at temperatures usually in excess of 300° C. One advantage in using the high temperature medium pressure lamps is that they are less susceptible to changes in fluid temperature. On the other hand, with low temperature low pressure UV lamps any significant change in water temperature can appreciably affect the operating temperature of the low pressure lamp and hence, affect its overall performance.

Higher intensity lamps, such as medium pressure mercury lamps are therefore preferred in this respect as discussed in U.S. Pat. No. 4,952,376. However, in view of the lamps being sealed within the protective sheath of the reactor, difficulties can be encountered in overheating of the lamps and possible deterioration as the lamp power increases. Other than cooling of the lamps as provided by fluid flowing over the protective sheaths, the temperature sensitive lamp end portions which include the electrical terminals are not adequately cooled and can from time to time overheat resulting in lamp failure. Such overheating problem with the higher temperature medium pressure lamps has therefore discouraged their use in UV treatment systems. As a result, lamps used in the system of U.S. Pat. No. 4,952,376 operate at the lower end of the temperature scale for medium pressure lamps and hence have less output compared to lamps operating at the higher end of the temperature scale.

Many commercially available systems function with the use of low temperature low pressure mercury lamps which have low power input usually in the range of 40 to 140 watts of UV power for each individual lamp. This power input usually equates to approximately 0.4–0.8 watts/cm of lamp arc length and operating temperatures less than 100° C. A commercial use of low power lamps for killing microorganisms in drinking water is described in U.S. Pat. No. 4,179, 616. Conventional G-37-T6 ultra-violet lamps are used which have an operating output in the range of 37 watts with an operating temperature well under 60° C. The primary use of the Coviello et. al. system is to produce optimum quantities of ozone by passing air through the system at a very low flow rate. The produced ozone is then transferred into a treatment tank to further sterilize the drinking water. Coviello et. al. contemplate the passage of air over the lamp ends, such as described with reference to FIGS. 3 and 5. The air is introduced under pressure and circulates at high velocity only over the lamp ends. The system of FIG. 4 of Coviello contemplates passage of air at a low flow rate over the lamp to optimize a generation of ozone, whereas apparently at the lamp end portions, the space is relatively constricted so that a higher flow rate is achieved over the lamp ends to effect cooling thereof. Although, these approaches to lamp end cooling may be suitable for low pressure lamps operating at relatively low temperatures normally less than a 100° C, such cooling systems are totally unsatisfactory for medium and high pressure lamps operating a temperatures in excess of 300° C.

There are several other disadvantages and drawbacks to the above systems for the treatment of contaminated fluids. Low pressure lamps have good efficiency (30%) which refers to the percent output of UV between 200 nm and 300 nm, which is the important UV region for decontaminating fluids. However, low pressure lamps have a major disadvantage since they are of such low input powers (40–120 watts typically) that a very large number of lamps are required for the treatment of fluids at high flow rates. This becomes impractical since many lamps and reactor chambers have to be built and maintained. Conventional medium pressure lamps are of low efficiencies, <20%, such that again too many lamps are required and the electrical consumption is high. There is thus a need for a lamp which operates at high power with good efficiency. There are now lamps available with high power inputs and efficiencies of around 30%. These lamps have higher input per unit length of arc than do the standard medium pressure lamps (100–300 watts/cm compared to <100 watts/cm). The lamps also run hot with bulb temperatures in the range of 600° C.–1000° C. These factors result in much more heat being generated at the quartz surfaces of the sleeve and lead to problems with cooling of the lamps and the surrounding materials of constructions.

In applicant's aforementioned U.S. Pat. Nos. 5,133,945 and 5,266,280, a cooling system is described for the high pressure lamps which operate at temperatures normally in excess of 600° C. Individual cooling fans are provided at each end of the reactor system to direct cooling air onto the ceramic mount for each lamp end. Each cooling fan has a duct for directing the cooling air at the ceramic mount to ensure that the electrodes sealed into the lamp ends do not degrade due to the high temperatures in the quartz of the lamp. Air which is directed at the lower portion of the lamp may enter the annular space between the protective sheath and the quartz lamp surface. Such circulating air is allowed to exit at the top of the reactor to further enhance the cooling of the system. Although this system is adequate for cooling of the high pressure lamps, it has been found that lamp operation is not always consistent and hence has been enhanced by the cooling system described in applicant's aforementioned U.S. patent application Ser. No. 07/836,617 filed Feb. 18, 1992.

The present invention provides an exhaust system for lamp cooling which not only improves lamp cooling but as well improves lamp operation and at the same time continues to provide protection for the surrounding materials supporting the lamp in the reactor.

SUMMARY OF THE INVENTION

According to an aspect of the invention an improved cooling system for high temperature UV lamps in a reactor assembly is provided. Accordingly, in a reactor assembly for destroying contaminants in fluids by the application of UV radiation to promote such destruction, the reactor assembly comprising i) a reactor column with an inlet at one end to introduce fluids to said reactor and an outlet at another end to remove treated fluids from said reactor, ii) a UV radiation emitting lamp operating at temperatures in excess of 300° C. and positioned in said reactor column, iii) a cylindrical protective sheath transparent to UV radiation for said lamp, said sheath being concentric with said lamp and isolating said lamp from said reactor interior, said reactor column having a wall defining a reactor space through which fluids to be treated flow from said reactor inlet through to said reactor outlet, whereby fluid flow over said sheath effects cooling of said sheath due to lamp heating, iv) each end of said sheath projecting through said reactor column wall and means for sealing each end of said sheath to said reactor wall whereby each end of said sheath opens outwardly of said reactor, said sealing means retaining thereby fluids in said reactor space;

v) said lamp having a first terminal portion and second terminal portion, said lamp being of sufficient length to extend said terminal portions beyond corresponding open ends of said sheath, vi) means for supporting each said terminal at a corresponding portion of said reactor wall, each of said support means having a lamp engaging portion which transverses said open ended sheath in a manner which provides air communication with sheath interior, vii) means for directing cooling air onto each of said first and second terminal portions to cool said terminal portions and thereby prevent deterioration of said lamp terminal portions due to excessive heating, said sheath having an internal diameter greater than an external diameter for said lamp, said means for directing cooling air onto said first terminal being adapted to develop an air pressure value at a corresponding first end of said sheath greater than an air pressure value at a corresponding second end of said sheath, whereby constant flow of cooling air is assured through said sheath and over said lamp by virtue of said sheath first and second ends being open outwardly of said reactor wall, such flow of cooling air being controlled to permit said lamp to operate at optimum operating temperatures, viii) the improvement comprising: an exhaust system for said means for directing cooling air, said exhaust system comprising an exhaust fan and ductwork adapted to draw cooling air over said first terminal portion, through said sheath and over said lamp toward said second terminal portion and to draw cooling air over said second terminal portion, said exhaust fan exhausting the cooling air gathered from said sheath and from said second terminal portion, said ductwork providing an air inlet to supplement cooling air drawn over said second terminal portion.

Further advantages and features of the invention will be apparent to those skilled in the art from the following detailed description thereof taken in conjunction with the accompanying drawings.

BRIEF DESCRIPTION OF THE DRAWINGS

Preferred embodiments of the invention are shown in the drawings wherein.

DETAILED DESCRIPTION OF THE PREFERRED EMBODIMENTS

Figure 1:
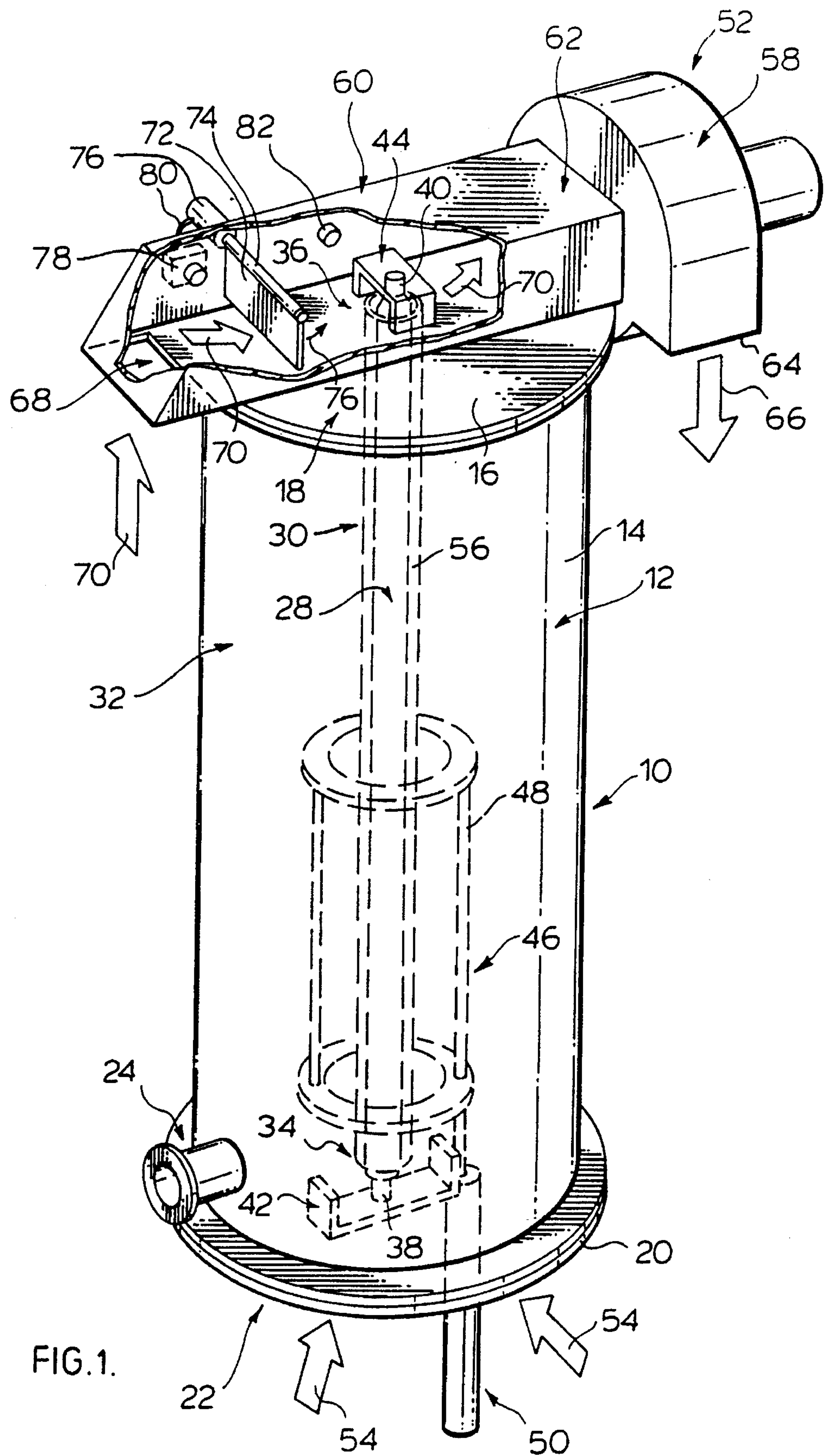
FIG. 1 is a top perspective view of a UV reactor system having the improved exhaust system for lamp cooling.

The reactor assembly lamp cooling of this invention is particularly adapted for use with medium and high pressure UV lamps. As will become apparent in the following discussion of the preferred embodiments, special provisions have been made in the reactor assembly to provide for fluid treatments while using high intensity UV lamps which operate at very high temperatures. In the industry of UV lamps it is generally understood that the lamps fall into three categories of low pressure, medium pressure and high pressure lamps. The pressure refers to the build up of vapour pressure within the lamp during operation. The pressure build up is normally due to the vaporization of mercury within the lamp. Usually exciting gases are contained in the lamp which commence the arc discharge and through the arc discharge the mercury is heated to vaporization temperature to produce a vapour in the lamp which in turn during excitation cycles emits the UV radiation of the desired intensity and wavelength. Low pressure lamps have lamp wattages of about 0.01 watts/cm$^2$ and operate at temperatures less than 100° C. As defined in the literature [L. R. Kohler "Ultraviolet Radiation" John Wiley & Sons Inc. New York 1965 and J. F. Waymouth "Electric Discharge Lamps, The MIT Press, Cambridge 1978 and R. Phillips "Sources and Applications of Ultraviolet Radiation" Academic Press, Toronto 1983 ] medium pressure lamps have lamp wattages around 0.1 to 1.0/cm$^2$ and normally operate at temperatures around 300° to 400° C. As already discussed, the embodiments of this invention are directed towards the use of the medium to high pressure lamps which operate at high temperatures normally in excess of 300° C. and usually in excess of 700° C. up to 1000° C. or even higher perhaps to 1100° C. At these high operating temperatures several aspects during their operation become a problem which have been solved by the cooling system described in applicant's aforementioned co-pending application Ser. No. 07/836,617 and are now further improved upon.

The preferred lamp for use in the system shown in the drawings is that sold by the applicant. Such UV lamps are high intensity, high pressure, mercury vapour lamps with about 30% of the UV radiation output below 300 nm. Most of the water decontamination processes carried out in this reactor are in accordance with processes proprietary to the applicant such as described in U.S. Pat. Nos. 4,956,098, 5,043,079 and 5,043,080. The greater the output below 300 nm the more effective the chemical decontamination treatment.

Several structural and operational details of the reactor assembly, internal baffles and lamp cleaning system are described in applicant's aforementioned U.S. Pat. Nos. 5,133,945, 5,266,280 and the aforementioned copending patent application Ser. No. 07/836,617, the subject matter of which is hereby incorporated by reference. Based on the detailed description provided in those earlier patents and patent applications, the operation of the reactor systems of the drawings should be readily apparent to those skilled in the art. However, to facilitate such understanding and for purposes of understanding the operation of the improved cooling system in accordance with this invention, a brief description of certain aspects of the reactor is herein provided.

The improved lamp cooling system of this invention draws air from two sources to ensure cooling of the tips of the UV lamp as well as proper cooling of the lamp body along its length. Lamps may be positioned in any orientation in the reactor or the reactor itself may be positioned in any desired orientation between horizontal and vertical. By virtue of the flexible lamp orientation, it is possible to provide a reactor column in which several high pressure lamps are provided. For example, for treating large flow rates of water, a single reactor housing a multitude of lamps can be used. Such bank of lamps further enhances the operating parameters of the reactor system for treating larger flowrates of water than can be treated with a reactor having a single lamp system. The lamp cooling air exhaust system in drawing from two sources ensures the correct amount of cooling air along the lamp, while at the same time providing sufficient cooling air for both lamps tips. The cooling air entering at least one of the air sources can be monitored to ensure correct continuous operation of the lamp cooling system. Furthermore, the positioning of the exhaust system at one end of the lamp greatly facilitates positioning of several lamps in a confined space of a reactor column to form the desired bank of UV lamps.

With reference to FIG. 1, the reactor assembly 10 comprises a reactor column 12 which is preferably cylindrical. It is appreciated, however, that the reactor may take on a variety of other shapes to optimize on space requirements and the like. The preferred cylindrical reactor has a reactor wall made up of the column sidewall 14 and end wall portion 16 of endplate 18 and wall portion 20 of endplate 22. The reactor column has an inlet 24 at one end to introduce fluids to the reactor and an outlet at the other end to remove treated fluids from the rector. The medium/high UV radiation emitting lamp 28 is provided in the reactor column. A cylindrical protective sheath 30 which is transparent to UV radiation is provided for the lamp. The sheath is concentric with the lamp and isolates the lamp from the reactor interior which is an annular space generally designated 32. The reactor column wall made up of portions 14, 16 and 20 define the reactor annular space 32 through which the fluids introduced via inlet 24 are treated as they flow from one end of the reactor to the other. Such fluid flow over the sheath effects cooling thereof as caused by the high temperature lamp. The ends of the sheath generally designated 34 and 36 project through the column wall portions 20 and 16 respectively. A suitable means is provided for sealing the sheath ends 34 and 36 to the column wall portions, details of which will be described with respect to FIG. 4. As a result with such sealing devices in place, each end of the sheath then opens outwardly of the reactor as shown more clearly in FIG. 2.

The UV lamp has a first terminal portion 38 and a second terminal portion 40 where the length of the lamp is sufficient to extend the terminal portions beyond the corresponding open ends 35 and 36 of the protective sheath 30. Brackets 42 and 44 act as means to support each terminal at a corresponding portion of the reactor wall as will be described with respect to FIG. 2. Each support bracket has a lamp engaging portion which traverses the open ended sheath in a manner which provides air communication with the sheath interior.

A lamp cleaning system 46 comprises a brush device 48, which is reciprocated along the sheath 30 by reciprocating piston 50 to effect desired cleaning of the sheath due to flowing thereof by fluids passing through the annular reactor chamber 32.

Cooling air is directed onto each of the first and second terminal portions 38 and 40 of the lamp by a cooling device generally designated 52. The device 52 draws air across the lower terminal portion 38 in the direction of arrows 54. The air passes upwardly of the sheath over the lamp 28 and outwardly over the terminal portion 40. The sheath has an internal diameter greater than the external diameter of the lamp to permit cooling air to pass through the annular space 56 where the cooling air is encouraged to travel through such space by developing an air pressure value at the first terminal end 38, which is greater than the air pressure value at the second terminal end 40. As a result of this air pressure difference, a constant flow of cooling air is assured through the sheath and over the lamp by virtue of the sheath first and second ends being open outwardly of the reactor wall. The constant flow of cooling air is controlled to permit the lamp to operate at optimum operating temperatures.

The improvement with respect to the cooling air device is the provision of an exhaust system 52 which comprises an exhaust fan 58 and complimentary ductwork 60. The exhaust fan 58 has an intake in region 62. Exhaust air drawn through the intake is exhausted via the outlet 64 in the direction of arrow 66. The flowrate through the exhaust fan 58 is sufficient to develop a lower pressure in the region of terminal 40 than in the region of terminal 38. Hence the desired pressure differential is established which causes air to flow over terminal 38 in the direction of arrow 54 and through the annular space 56 between the sheath and the lamp. The ductwork 60 also includes an opening 68 which provides supplemental cooling air to be drawn over the second terminal portion 40 in the direction of arrows 70. An air inlet 73 beneath baffle 72 is defined by the crosssectional space in the ductwork that is blocked off by the baffle. The air inlet 73 is designed to ensure proper flowrates of cooling air through annular space 56 to optimize lamp temperature and hence UV radiation input to fluids flowing through reactor space 32. The baffle 72 may be fixed to define a desired cross-sectional area for the inlet 73 for the supplemental cooling air. Alternatively the baffle 72 may be pivoted about rod 74 such that it swings upwardly in the direction of arrow 76. Such pivoting of the baffle 72 accommodates variations in the exhaust fan speed which may be due to power surges, ambient temperature changes and the like. A sensor 76 may be connected externally to rod 74 to sense rotation of the rod 74. The sensor 76 is electrically connected to signal generator 78 by wire 80. The signal generated by device 78 may be transmitted by wire or otherwise to a monitoring system which can monitor the efficiency of the exhaust fan 58 by virtue of the degree of tilt or pivoting of the baffle 72. Furthermore, the device 78 can indicate a malfunction of the fan 58 should it be operating at such low efficiencies that the baffle 72 is not sufficiently pivoted or not pivoted at all due to very low or lack of air movement in the direction of arrow 70. In the event that the baffle 72 is fixed and not allowed to pivot, operation of the fan may also be detected by an airflow sensor 82 which is connected to a suitable signal generator not shown, to transmit a signal to a monitor which determines absence or presence of airflow through the ductwork over the lamp end 40.

Figure 3:
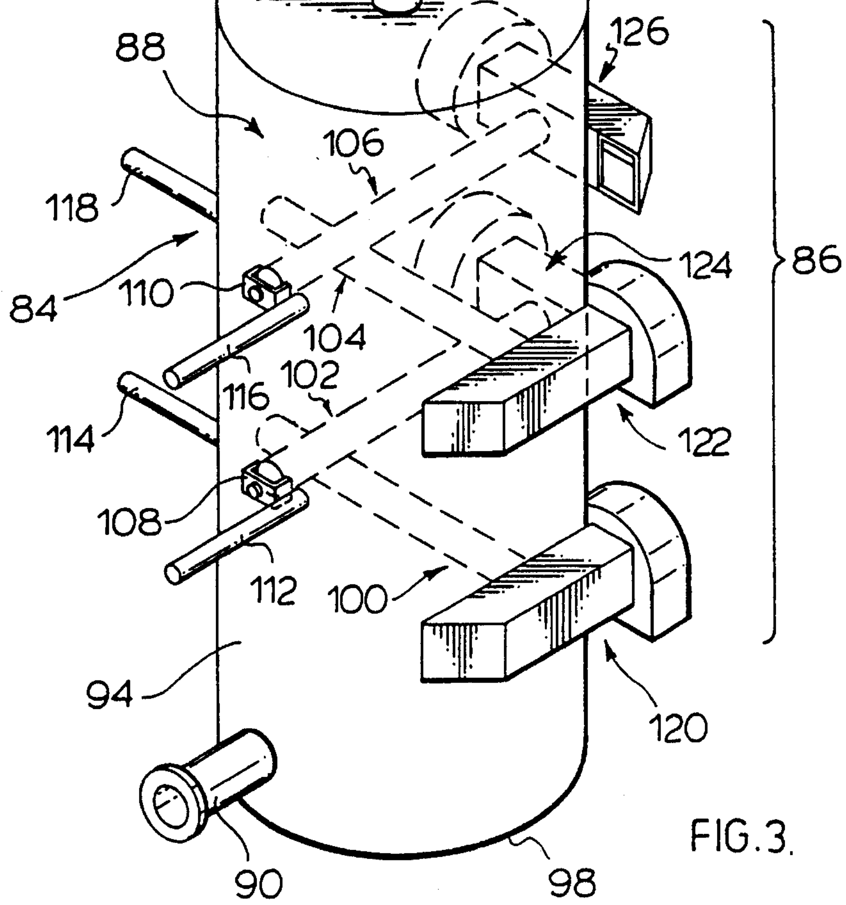
FIG. 3 is a schematic perspective of an alternative embodiment for the reactor system wherein a plurality of lamps are provided in a single reactor column, which may be either vertically or horizontally oriented.

The alternative reactor system 84 is shown in FIG. 3 where a bank of lamps 86 is provided in the reactor column 88. The reactor column 88 has an inlet 90 and outlet 92 so that fluids to be treated flow through the reactor space defined within the reactor walls of the column sidewall 94 and column end portions 96 and 98. The compact nature of each lamp with its corresponding lamp cooling system generally designated 100, 102, 104 and 106 facilitates relatively close positioning of the lamps without the lamp cooling devices interfering with one another. The lamps may be placed in the reactor column 88 in the cris-cross fashion shown in FIG. 3 or in view of the cooling system for the lamps allowing any orientation for the lamps, they may be positioned in a variety of other configurations within the reactor column 88.

Each lamp unit 102, 104 and 106 comprises the same components described with respect to FIG. 1, namely, a lamp, a protective lamp sheath and mounting devices for the lamp terminal ends. Some of the mounting devices are shown in FIGS. 3 and identified by numerals 108 and 110. Correspondingly pneumatic cylinders for reciprocating the sheath cleaning devices are identified at 112, 114, 116 and 118. The lamp cooling exhaust systems are generally designated 120, 122, 124 and 126. The exhaust systems are the same in construction as that described with respect to FIG. 1 and operate in the same manner to ensure proper flow of cooling air over the lamp tips and over the lamp body. By virtue of the exhaust systems operating independently for each lamp and being positioned solely at one end of the lamp, the aforementioned compact array of any orientation for the lamps may be achieved. It should be noted however, that in the ductwork of each cooling system, the baffle such as discussed, with respect to FIG. 1 and identified at 72, if it is to be pivoted, will have to be suspended about a horizontal axis within each respective ductwork for devices 120, 122, 124 and 126. With respect to the embodiment of FIG. 3, where the lamps are horizontally positioned, it is therefore appreciated that the rod 74 about which each baffle 72 would be pivoted, is also extending within the ductwork in a horizontal direction.

Figure 4:
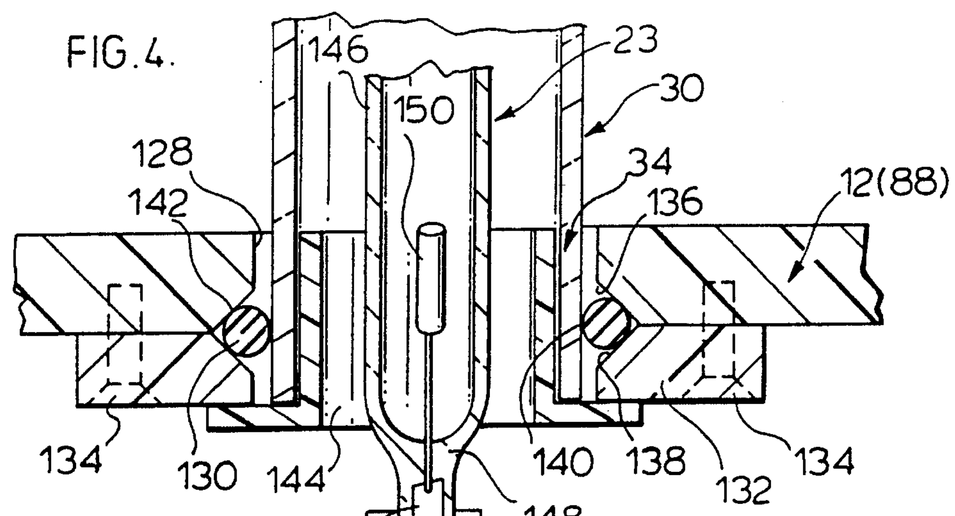
FIG. 4 is a detailed section showing the sealing of a lamp sheath in the reactor wall of FIG. 3 or in the reactor end of FIG. 2.

Details of the manner in which the sheath is sealed to the reactor wall which may be a portion of the end wall or side wall of the reactor configurations of FIG. 1 and 3, are shown in FIG. 4. The protective sheath 30 has its end portion 34 extending through the reactor wall 12 which as already noted may be the sidewall 88 of the reactor 84 of FIG. 3 or an end wall 16 or 20 of the reactor 10 of FIG. 1. A hole 128 is provide in the reactor wall and having an inside diameter greater than the outside diameter of the sheath 30. This allows for placement as well as expansion of the sheath during operation of the system. In order to seal the sheath end 34 relative to the reactor wall 12, an O-ring seal 130 is provided about the perimeter of the end portion 34. In order to compress the O-ring seal 130 about the perimeter of the end portion 34 and as well against the reactor wall 12, a clamp ring 132 is bolted to the reactor wall by bolts 134. The O-ring 130 is then compressed between opposing converging faces 136 and 138 to ensure a seal at O-ring interfaces 140 and 142. Preferably the O-ring 130 is made of a temperature, UV radiation and ozone resistant material such as that sold under the trade-mark VITON™. To ensure prolonged life for the O-ring particularly if made from material which may not be resistant, a ceramic collar 144 is positioned within the end 34 of the sheath 30. The ceramic collar blocks UV radiation and as well insulates the O-ring from the high temperature lamp 28. As to the lamp 28, it has the usual quartz lamp body 146 which is pinched closed at 148 for terminal end 38. An electrode 150 is provided within the lamp end to which a link in the form of a metal ribbon 152 is connected. The link 152 is connected by wire 154 which passes through the ceramic lamp end 156 to an appropriate source of electrical power. The metal link 152 deteriorates when its temperature exceeds approximately 350° C. It is therefore desirable to ensure that the lamp cooling system provides for sufficient lamp cooling so that the lamp end temperature does not exceed 350° C.

Several considerations are necessary in providing for cooling of the lamp ends as well as the lamp body housed within the protective sheath 30. In cooling the lamp ends it is important not to overcool the lamp body as housed within the sheath 30. Overcooling of the lamp body results in decreased lamp performance and can even result in extinguishing the lamp. Extinction of lamp operation usually happens when the lamp body is cooled to the extent that vapour being formed by the electric discharge is caused to immediately condense so that the lamp never gets beyond the start-up phase or during operation is cooled to the extent that the mercury vapour condenses within the lamp. It is also important to ensure that any temperature sensitive portions of the reactor body be designed in a manner so as not to be affected by the high temperature operation of the lamp or that the portions of the reactor assembly exposed to UV radiation are of suitable materials or are protected from UV deterioration.

Another factor which enters into the design considerations is protecting users from exposure to UV radiation during lamp operation. This necessitates enclosing both the lower and upper portions of the reactor so that operators cannot view directly UV radiation emitted by the lamp. It is appreciated of course that components of the reactor may be made of materials which do not reflect UV radiation so that it is only direct radiation exposure which could cause a problem with operators. Each end of the reactor maybe enclosed in a support base or shielded. The support base may have a door access for purposes of servicing the pneumatic cylinder and as well facilitate lamp replacement. Suitable interlocks are provided such that when the door to the support base is opened, the lamp is shut down to avoid exposure to UV radiation and possible electric shock.

Similarly, end 18 of the reactor has to be enclosed by a suitable enclosure connected to the outlet ductwork 60 of the exhaust system 52. The ductwork 60 prevent operators from having direct eye access to radiation emitted by the lamp 28.

Figure 2:
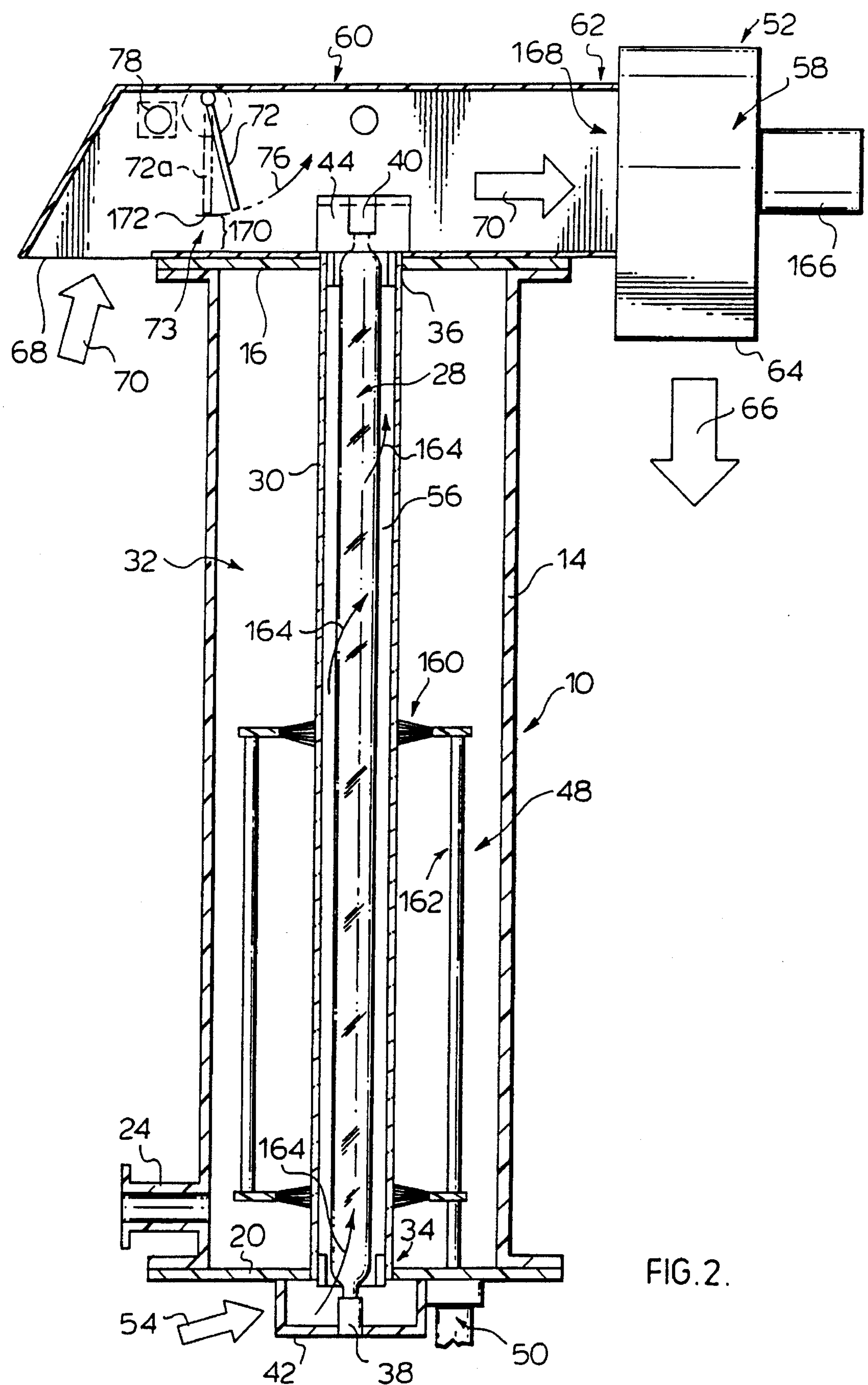
FIG. 2 is an elevational cross-sectional view of the reactor of FIG. 1.

The operation of the improved lamp cooling system is described in detail with respect to FIG. 2. The reactor 10 can be vertically or horizontally positioned or oriented at any angle therebetween. The inlet 24 and the outlet are provided in the reactor sidewall 14. The reactor space 32 is sealed off at the reactor ends by end plate wall portions 16 and 20. The annular space 32 is defined between the outer circumference of the protective sheath 30 and the inside of the walls 14, 16 and 20. Fluids which flow through the reactor space 32 tend to fowl the exterior surface of the sheath. A brush system 160 is connected to the carriage 162 of the cleaning system 48 as described with respect to applicant's U.S. Pat. Nos. 5,133,945 and 5,266,280. The cleaning system functions in a manner to keep the outer surface of the sheath clean so that the full effectiveness of the UV radiation generated by the lamp 28 is received by the fluid flowing through reactor space 32.

As described with respect to FIGS. 2 and 4, the sheath ends 34 and 36 are open to the outside of the reactor. This allows cooling air to flow freely through the annular space 56, between the lamp 28 and the sheath 30. Such flow of cooling air through that annular space is represented by arrows 164. The fan 58 as driven by motor 166 has its intake 168 at the one end 62 of the ductwork 60. The fan 58 discharges air from its outlet 64 in the direction of arrow 66 at a sufficient flowrate to develop as previously described a significant pressure drop over the length of the lamp between ends 34 and 36 of the sheath. The low pressure developed by the fan at end 36 draws air into the open end of the sheath and into annular passage 56 via outside air entering in the direction of arrow 64. The bracket 42 for the lamp end is U-shaped so as to not impede the flow of air into the open end of the sheath, so that air can travel freely along the annular passageway 56. The ductwork 60 includes a supplemental air intake 68, the flow through which is controlled by baffle 72. Air entering in the direction of arrow 70 flows underneath baffle 72 and over terminal 40 of the lamp. Terminal 38 is cooled by the air flowing in direction of arrow 54 and into the annular space. The lamp body is cooled by such air flowing along the annular space and then terminal 40 is cooled primarily by supplemental air flowing underneath baffle 72 and across the terminal 44. The air flowing out of annular space 56 through open end 36 may also affect cooling of the lamp terminal. The bracket 44 is oriented in a direction so that the air flow from underneath the baffle 72 flows directly onto the terminal 40.

The air intake for the fan 58 draws air not only from the annular space between the sheath and the lamp but as well from the opening 68 and through the supplemental air intake 73. The extent to which the fan draws air from the supplemental air intake is controlled by the positioning of baffle 72. The fixed position for the baffle is shown at 72A where its space above the base of the ductwork is indicated at 170. The positioning of the lower end 172 of the baffle can be determined by trial and error where it is understood that if the spacing 170 is too large, lamp cooling may be jeopardized, whereas, if the spacing 170 is too small, then the lamp cooling may be too great. For example, it has been found that for an annular space having as cross-sectional area of approximately 4.25 square inches in region 56, a fan flow rate of 245 CFM and ductwork 60 having a cross-sectional area in the region of baffle 72 of 7"×5" and a baffle size of 7"×2" the spacing 170 is in the range of 2" to 3". This provides approximately 30% to 70% of the air drawn into the fan 58. With the supplemental air making up 30% of the total air exhausted by fan 58, a considerably higher flowrate is achieved through the annular space 56 versus supplemental air making up 70% of the air exhausted. Such range takes into consideration the operating temperatures of the lamp, the temperature of the fluids being treated and the ambient temperature and pressure in which the system is operated.

It is also appreciated that the baffle 72 may pivot in the manner described with respect to FIG. 1. Such pivotal action in the direction of arrow 76 takes into consideration varying ambient conditions. There may be power surges which causes the motor 166 to speed up and hence exhaust considerably more air. In that situation if the baffle 72A is rigid then considerably more air will be drawn in through the annular space 56 via the sheath open end 34. This may result in excessive cooling of the lamp and decrease in function. However, as shown in FIG. 2, if the baffle 72 is allowed to pivot in the direction of arrow 76, a power surge and speed up of the motor 166 can be accommodated by the moveable baffle. As the baffle swings upwardly in the direction of arrow 76, space 170 increases to allow more supplemental air to enter and reduce to some extent the pressure differential across the annular space 56. Such movement thereby dampens to some extent excessive increased air flow through the annular space 56 which could impact on the lamp efficiency by virtue of excessive cooling. Correspondingly, should the fan efficiency drop due to a loss of power or physical damage to the fan, the flowrate through the fan decreases. This allows the baffle 72 to pivot in a direction opposite to arrow 76 to thereby decrease the space 170 and as a result decrease the flowrate of supplemental air brought into the system, so that air drawn through annular space 56 continues at the desired flowrate so that lamp overheating is avoided. Pivoting in either direction, however, of baffle 72 can also be caused as already mentioned by change in ambient pressure, temperature or other variables which might affect the flow of air.

The improved lamp cooling system in accordance with this invention substantially enhances the UV radiation system for destroying contaminants in fluids. The lamp may be positioned in any desired orientation to accommodate a full range of reactor positionings as well positioning of the lamps within the desired reactor configuration. Reactors may now take on a variety of shapes to accommodate physical plant peculiarities or reactor plug flow design to maximize reaction volume in a minimum of reactor space. By use of the supplemental air drawn through the annular space between the lamp and the sheath, overcooling of the lamp ends and lamp body is avoided. Variables in the ambient can also be readily accommodated by baffle design within the ductwork. By ensuring proper cooling of the lamp body, lamp performance is optimized by avoiding hot spots along the lamp body length. By having the fan cooling system at one end of the lamp arrangement, maintenance of the reactor system as well as replacement of the quartz lamps is facilitated. The position of the exhaust fan is opposite the supplemental air intake to ensure that the cooling air flows directly over the second terminal portion of the lamp which extends beyond the open end of the protective sheath.

Although preferred embodiments of the invention are described herein in detail, it will be understood by those skilled in the art that variations may be made thereto without departing from the spirit of the invention or the scope of the appended claims.

We claim:

1. In a reactor assembly for destroying contaminants in fluids by the application of UV radiation to promote such destruction, said reactor assembly comprising:

i) a reactor column with an inlet at one end to introduce fluids to said reactor and an outlet at another end to remove treated fluids from said reactor, ii) a UV radiation emitting lamp operating at temperatures in excess of 300° C. and positioned in said reactor column, iii) a cylindrical protective sheath transparent to UV radiation for said lamp, said sheath being concentric with said lamp and isolating said lamp from said reactor interior, said reactor column having a wall defining a reactor space through which fluids to be treated flow from said reactor inlet through to said reactor outlet, whereby fluid flow over said sheath effects cooling of said sheath due to lamp heating, iv) each end of said sheath projecting through said reactor wall and means for sealing each end of said sheath to said reactor wall whereby each end of said sheath opens outwardly of said reactor, said sealing means retaining thereby fluids being treated in said reactor space, v) said lamp having a first terminal portion and second terminal portion, said lamp being of sufficient length to extend said terminal portions beyond corresponding open ends of said sheath, vi) means for supporting each said terminal at a corresponding portion of said reactor wall, each of said support means having a lamp engaging portion which transverses said open ended sheath in a manner which provides air communication with sheath interior, vii) means for directing cooling air onto each of said first and second terminal portions to cool said terminal portions and thereby prevent deterioration of said lamp terminal portions due to excessive heating, said sheath having an internal diameter greater than an external diameter for said lamp, said means for directing cooling air onto said terminals being adapted to develop an air pressure value at a corresponding first end of said sheath greater than an air pressure value at a corresponding second end of said sheath, whereby a constant flow of cooling air is assured through said sheath and over said lamp by virtue of said sheath first and second ends being open outwardly of said reactor wall, such constant flow of cooling air being controlled to permit said lamp to operate at optimum operating temperatures, viii) the improvement comprising: an exhaust system for said means for directing cooling air, said exhaust system comprising an exhaust fan and ductwork adapted to draw cooling air over said first terminal portion, through said sheath and over said lamp toward said second terminal portion and to draw cooling air over said second terminal portion, said exhaust fan exhausting the cooling air gathered from said sheath and from said second terminal portion, said ductwork providing an air inlet to supplement cooling air drawn over said second terminal portion.

2. In a reactor assembly of claim 1, said ductwork comprising a baffle which determines cross-sectional area of said air inlet.

3. In a reactor assembly of claim 1, said baffle being pivotally mounted in said ductwork, said baffle pivoting as air flow through said air inlet increases, to enlarge thereby cross-sectional area of said air inlet in relation to rate at which said exhaust fan draws air.

4. In a reactor assembly of claim 3, a sensor for detecting extent of baffle pivot to monitor thereby rate of exhaust fan air draw.

5. In a reactor assembly of claim 1, said exhaust fan having an intake laterally offset from said second terminal portion and opposite said air inlet which is laterally offset from said second terminal portion whereby supplement cooling air flows over said second terminal portion.

6. In a reactor assembly of claim 1, said reactor column is cylindrical and coincident with said protective sheath, such fluids flowing along said sheath between said inlet and said outlet.

7. In a reactor assembly of claim 1, a plurality of said protective sheaths extending across said reactor column and being spaced apart along said column, a separate exhaust system being provided at said second end of each said sheath.

8. In a reactor assembly of claim 6, an end cap being provided at each end of said reactor column and constituting part of said reactor wall, said sheath extending through each respective end cap and said sealing means sealing said sheath to said wall portion of said end cap.

9. In a reactor assembly of claim 5, said ductwork being an elongate housing with said air inlet being on one side of said housing and said fan air intake being on the other side of said housing, said housing shielding said second terminal portion.

10. In a reactor assembly of claim 1, said lamps and sheaths being mounted either vertically or horizontally.

11. In a reactor assembly of claim 7, said lamps and sheaths being mounted either vertically or horizontally,

* * * * *